United States Patent
Naser et al.

(10) Patent No.: US 12,138,037 B2
(45) Date of Patent: Nov. 12, 2024

(54) DEVICE, SYSTEM, AND METHOD FOR ASSESSING SLEEP DISORDERS

(71) Applicant: DORMOTECH MEDICAL LTD., Kochav Yair (IL)

(72) Inventors: Abd El-Kader Naser, Tira (IL); Ofer Barnea, Herzliya (IL); Shlomo Zucker, Mikhmoret (IL)

(73) Assignee: DORMOTECH MEDICAL LTD., Kochav Yair (IL)

( * ) Notice: Subject to any disclaimer, the term of this patent is extended or adjusted under 35 U.S.C. 154(b) by 0 days.

(21) Appl. No.: 17/841,738

(22) Filed: Jun. 16, 2022

(65) Prior Publication Data
US 2022/0304591 A1 Sep. 29, 2022

Related U.S. Application Data

(63) Continuation of application No. 16/302,104, filed as application No. PCT/IB2017/000667 on May 17, 2017, now Pat. No. 11,369,284.

(Continued)

(51) Int. Cl.
*A61B 5/08* (2006.01)
*A61B 5/00* (2006.01)
*A61B 5/0205* (2006.01)
*A61B 5/087* (2006.01)
*A61B 5/1455* (2006.01)
(Continued)

(52) U.S. Cl.
CPC .......... *A61B 5/0878* (2013.01); *A61B 5/0006* (2013.01); *A61B 5/0008* (2013.01); *A61B 5/0205* (2013.01); *A61B 5/14551* (2013.01); *A61B 5/389* (2021.01); *A61B 5/398* (2021.01);
(Continued)

(58) Field of Classification Search
None
See application file for complete search history.

(56) References Cited

U.S. PATENT DOCUMENTS

| 4,195,626 A | 4/1980 | Schweizer |
| 5,335,659 A | 8/1994 | Pologe |

(Continued)

FOREIGN PATENT DOCUMENTS

| EP | 2636370 A2 | 2/2013 |

OTHER PUBLICATIONS

Storck K et al: "Heat Transfer Evaluation of the Nasal Thermistor Technique", IEEE Transactions on Biomedical Engineering, IEEE Service Center, Piscataway, NJ, USA, vol. 43, No. 12, Dec. 1, 1996 (Dec. 1, 1996), pp. 1187-1191, XP000658965, ISSN: 0018-9294, DOI: 10.1109/10.544342.

(Continued)

*Primary Examiner* — Etsub D Berhanu
(74) *Attorney, Agent, or Firm* — The Roy Gross Law Firm, LLC; Roy Gross

(57) ABSTRACT

Methods, systems, and devices for assessing breathing disorders such as apneas and hypopneas are provided. An airflow monitoring device can be positioned in thermal communication with respiratory airflow (nasal and/or oral airflow). The airflow monitoring device can include a thermistor configured to measure heating and cooling cycles of respiratory airflow and determine respiratory airflow velocity from analysis of thermistor cooling. This velocity, alone or in combination with other physiological parameters, such as blood oxygen saturation, respiration effort, heart rate, body movement, etc. can be employed to assess sleep disorders.

10 Claims, 9 Drawing Sheets

Related U.S. Application Data

(60) Provisional application No. 62/337,408, filed on May 17, 2016.

(51) Int. Cl.
*A61B 5/389* (2021.01)
*A61B 5/398* (2021.01)

(52) U.S. Cl.
CPC .......... *A61B 5/4818* (2013.01); *A61B 5/6819* (2013.01); *A61B 2560/0406* (2013.01)

(56) References Cited

U.S. PATENT DOCUMENTS

| | | |
|---|---|---|
| 5,413,111 A | 5/1995 | Wilkinson |
| 6,368,287 B1 | 4/2002 | Hadas |
| 2003/0176803 A1 | 9/2003 | Gollar |
| 2007/0123756 A1 | 5/2007 | Kitajima et al. |
| 2011/0197689 A1 | 8/2011 | Haveri et al. |
| 2011/0201956 A1 | 8/2011 | Alferness et al. |
| 2012/0226182 A1 | 9/2012 | Bonato et al. |
| 2014/0005557 A1 | 1/2014 | Rich |
| 2014/0275930 A1 | 9/2014 | Rich |

OTHER PUBLICATIONS

Farré, et al. ("Accuracy of thermistors and thermocouples as flow-measuring devices for detecting hypopnoeas," Eur. Respir. Journal, 11, pp. 179-182, 1998).

BaHammam ("Comparison of Nasal Prong Pressure and Thermistor Measurements for Detecting Respiratory Events during Sleep," Respiration, 71, pp. 385-390, 2004).

Noto et al., "Automated analysis of breathing waveforms using BreathMetrics: a respiratory signal processing toolbox", Chemical Senses, 2018, vol. 43, 583-597. Retrieved Dec. 22, 2021; doi: 10.1093/chemse/bjy045.

DEVICE, SYSTEM, AND METHOD FOR ASSESSING SLEEP DISORDERS

CROSS-REFERENCE TO RELATED APPLICATIONS

This application is a continuation of U.S. Ser. No. 16/302,104 filed Nov. 18, 2018, which is a National Phase entry of PCT/IB2017/00667 filed on May 17, 2017, which claims the benefit of U.S. Provisional Patent Application No. 62/337,408, filed May 17, 2016, and entitled "DEVICE, SYSTEM, AND METHOD FOR ASSESSING SLEEP DISORDERS." The contents of these applications are all incorporated by reference in their entirety.

FIELD

Embodiments of the present disclosure relate to devices, systems, and methods for assessing sleep disorders.

BACKGROUND

When a person is awake, muscles associated with breathing (e.g., muscles of the nose, throat, and mouth) can move to maintain the upper respiratory tract (e.g., nose and nasal passages, pharynx, and oral cavity) open to airflow and allow normal breathing. However, when a person falls asleep, these muscles can relax and block airflow through the upper respiratory tract. Such blockage is undesirable, as it can lead to breathing disorders associated with various health issues, including hypertension, stroke, irregular heartbeat, and heart attack. Breathing disorders during sleep have also been linked to a variety of other conditions such as reduced cognitive function due to the loss of sleep.

Breathing disorders during sleep can be divided into two categories, central and obstructive. In central disorder, the brain can fail to initiate neural impulses that activate the lungs. Obstructive disorder can further be subdivided into apneas and hypopneas. Obstructive sleep apnea can be characterized as a temporary absence or cessation of breathing that occurs during sleep for a period of over about 10 seconds due to complete blockage of airflow. As an example, sleep apnea can arise from airflow blockage due to relaxation of the tongue during sleep. Apnea can occur hundreds of times during a single night and it can lead to severe sleep disruption and excessive daytime fatigue or sleepiness.

Hypopnea can be described as a temporary decrease in inspiratory airflow relative to a person's effort or metabolic needs. In contrast to apnea, hypopnea is not a complete cessation of airflow for at least 10 seconds. Rather it can be described as a reduction of at least 30% of airflow for at least 10 seconds, resulting in decreased oxygen saturation. Hypopnea can arise from any condition that leads to partial airflow blockage during sleep. Examples can include acute tonsillitis, adenoiditis, congenital defects (e.g., nasal septum deformation), neuromuscular disease, and muscular dystrophy.

Sleep disorders have traditionally been assessed by patient observations taken in a sleep lab environment. The sleep lab can provide a controlled environment for measurement of a variety of different physiological parameters of a patient. Analysis of these measured physiological parameters can be employed to produce a "hypnogram" that describes the nature of the patient's sleep. Indices obtained from the hypnogram, such as apnea index (AI), apnea/hypopnea index (AHI), and a leg movement index, can then be used by a sleep specialist to diagnose sleep disorders in the patient.

While sleep lab studies are generally considered to be the standard for assessing sleep disorders, they can be problematic. Notably, because sleep lab studies are performed in a hospital or other clinical setting, they can fail to accurately reflect a patient's natural sleep environment, potentially leading to false diagnoses of sleep disorders, either positive or negative. In addition, patients are usually reluctant to sleep in the sleep lab and the cost is significant.

SUMMARY

In an embodiment, a respiratory airflow monitoring device is provided. The respiratory airflow monitoring device can include a body, a pair of first arms, and a first thermistor. The pair of first arms can extend distally outwards from the body. The first thermistor can be mounted to the body or at least one of the pair of first arms. At least one of the first arms can be moveable with respect to the other by a distance sufficient to position a human nasal septum therebetween. At least one of the first arms can be biased towards the other such that, when a human nasal septum is received between the pair of first arms, the pair of first arms can apply a compressive force to the nasal septum sufficient to retain the pair of first arms substantially in place.

In another embodiment of the airflow monitoring device, when a human nasal septum is received between the pair of first arms, the pair of first arms can apply a compressive force to the nasal septum sufficient to retain the pair of first arms substantially in place without additional support.

In another embodiment of the airflow monitoring device, the first thermistor can be mounted at a location such that, when a human nasal septum is received between the pair of first arms, the first thermistor can be in thermal communication with airflow expired and inspired through a nostril defined by the human nasal septum.

In another embodiment, the airflow monitoring device can also include a computing device in communication with the first thermistor and it can be configured to determine a velocity of nasal airflow based upon temperature measurements of nasal airflow acquired by the first thermistor.

In another embodiment, the airflow monitoring device can also include a second arm extending proximally outwards from the body and a second thermistor mounted to the second arm.

In another embodiment of the airflow monitoring device, the second arm can be dimensioned such that, when a human nasal septum is received between the pair of first arms, the second thermistor is positioned in thermal communication with oral airflow.

In another embodiment, the airflow monitoring device can also include a computing device in communication with the second thermistor and it can be configured to determine a velocity of oral airflow based upon temperature measurements of oral airflow acquired by the second thermistor.

In another embodiment of the airflow monitoring device, the pair of arms can be configured such that the compressive force applied to a nasal septum received therebetween is less than a threshold compressive force that damages the nasal septum.

In another embodiment of the airflow monitoring device, the body can include two halves configured to couple together, where one of the first arms can extend distally from a first half of the body and the other of the first arms can extend distally from a second half of the body.

In another embodiment of the airflow monitoring device, the thermistor can have a time constant selected from the range between about 3 seconds and about 10 seconds.

In a further embodiment, an airflow monitoring device can be provided. The airflow monitoring device can include a body, a pair of first arms, and a thermistor. The body can be configured to engage a support structure capable of being secured to a human head. The pair of first arms can extend distally outwards from the body. The first thermistor can be mounted to at least one of the body and the pair of first arms. The first arms can be offset from one another by a distance sufficient to allow a human nasal septum to be positioned therebetween. When a human nasal septum is received between the pair of first arms and the body is engaged by the support structure, a terminal end of each of the pair of first arms can be located within respective nostrils adjacent the nasal septum and the first thermistor can be in thermal communication with nasal airflow.

In another embodiment, the airflow monitoring device can also include an auxiliary monitoring device configured to couple to the support structure and measure one or more physiological parameters of a patient when the support structure engages a human head.

In another embodiment, the airflow monitoring device can also include a computing device in communication with the first thermistor and configured to determine a velocity of nasal airflow based upon temperature measurements of nasal airflow acquired by the first thermistor.

In another embodiment of the airflow monitoring device, the computing device can be in communication with the auxiliary monitoring device and it can be configured to identify a sleep disorder based upon the determined velocity of nasal airflow and a physiological parameter measured by the auxiliary monitoring device.

In another embodiment, the airflow monitoring device can also include a second arm extending proximally outwards from the body and a second thermistor mounted to the second arm.

In another embodiment of the airflow monitoring device, the second arm can be dimensioned such that, when a human nasal septum is received between the pair of first arms, the second thermistor can be positioned in thermal communication with oral airflow.

In another embodiment, the airflow monitoring device can also include a computing device in communication with the second thermistor and configured to determine a velocity of oral airflow based upon temperature measurements of oral airflow acquired by the second thermistor.

In another embodiment of the airflow monitoring device, the computing device can be in communication with the auxiliary monitoring device and it can be configured to identify a sleep disorder based upon the determined velocity of oral airflow and a physiological parameter measured by the auxiliary monitoring device.

In another embodiment of the airflow monitoring device, the thermistor can have a time constant selected from the range between about 3 seconds and about 10 seconds.

In another embodiment, a method for determining a velocity of respiratory airflow of a patient is provided. The method can include positioning a thermistor in fluid communication with respiratory airflow. The method can also include allowing the thermistor to undergo heating due to a flow of expired respiratory airflow. The method can additionally include measuring a temperature, T, of the thermistor while the thermistor is cooled due to a flow of inspired respiratory airflow at a temperature $T_A$. The method can additionally include determining a velocity of respiratory airflow based upon the measured temperature of the thermistor T and the temperature of the inspired respiratory airflow $T_A$.

In an embodiment of the method, the thermistor can be positioned within a nostril and the respiratory airflow is nasal airflow.

In an embodiment, the method can also include positioning the thermistor with respect to the nostril by compression against a nasal septum defining at least a portion of the nostril.

In an embodiment, the method can also include positioning the thermistor with respect to the nostril by support from an elastic band engaged with a head of the patient.

In an embodiment of the method, the thermistor can be placed in fluid communication with oral airflow.

In an embodiment of the method, the thermistor can have a time constant selected from the range between about 3 seconds and about 10 seconds.

In an embodiment of the method, the velocity of respiratory airflow can be further determined from measurement of a rate of change of temperature of the thermistor, $\dot{T}$.

In an embodiment of the method, the velocity of respiratory airflow can be determined empirically according to:

$$v = \sqrt[c]{\frac{1}{b}\left(\frac{-C_T \dot{T}}{(T-T_A)} - a\right)}$$

where a, b, and c are constants and $C_T$ is the heat capacity of the thermistor.

In an embodiment of the method, the velocity of respiratory airflow can be determined empirically according to:

$$G(v) = \frac{\dot{T}}{(T_A - T)}$$

where G(v) can be obtained experimentally.

BRIEF DESCRIPTION OF THE DRAWINGS

Embodiments of the present disclosure are described herein, by way of example only, with reference to the accompanying drawings. With specific reference now to the drawings in detail, it is stressed that the particulars shown are by way of example and for purposes of illustrative discussion of embodiments of the present disclosure only, and are presented in order to provide what is believed to be the most useful and readily understood description of the principles and conceptual aspects. In this regard, no attempt is made to show structural details of the disclosed embodiments in more detail than is necessary for a fundamental understanding, the description taken with the drawings making apparent to a person skilled in the art how the several forms of the disclosed embodiments can be embodied in practice.

DETAILED DESCRIPTION

Devices for assessing sleep disorders in a home environment have been developed but are problematic.

One approach has been to simulate the sleep lab environment in the home setting. As an example, prior to sleep, a subject can be attached to a recording device that records signals from a variety of sensors. However, such devices can be cumbersome, requiring the patient to be attached to the sensors at different locations on their body prior to sleep. These systems can also require the presence of a technician, as attachment of sensors to a patient can be complicated and require professional knowledge.

Another approach to studying sleep disorders can employ measurement of airflow (e.g., oral and/or nasal airflow) by use of a temperature-sensitive device placed in the airflow path of the nose and/or mouth. One example of a temperature-sensitive device is a thermistor, which is a device that can exhibit changes in electrical resistance with changes in temperature. When the patient breathes in or out, air can flow across the thermistor and it can change the thermistor temperature, resulting in a change in thermistor resistance. Thus, by measuring thermistor resistance over time, airflow due to the temperature changes arising from patient respiration can be inferred.

However, the use of thermistors as airflow measurement tools for assessment of apnea and/or hypopnea has been questioned and criticized in academic literature. In one example, Farré, et al. ("Accuracy of thermistors and thermocouples as flow-measuring devices for detecting hypopnoeas," *Eur. Respir. Journal,* 11, pp. 179-182, 1998) studied the use of thermistors and thermocouples as airflow measuring devices and concluded that they are inaccurate when used at the airflow conditions typical of sleep studies. In another example, BaHammam ("Comparison of Nasal Prong Pressure and Thermistor Measurements for Detecting Respiratory Events during Sleep," *Respiration,* 71, pp. 385-390, 2004) examined the use of thermistors and thermocouples in sleep studies and concluded that there was genuine concern in using thermistors or thermocouples for assessing oral and/or nasal airflow during sleep because they can fail to detect hypopneas or increased upper airway resistance.

Figure 1:
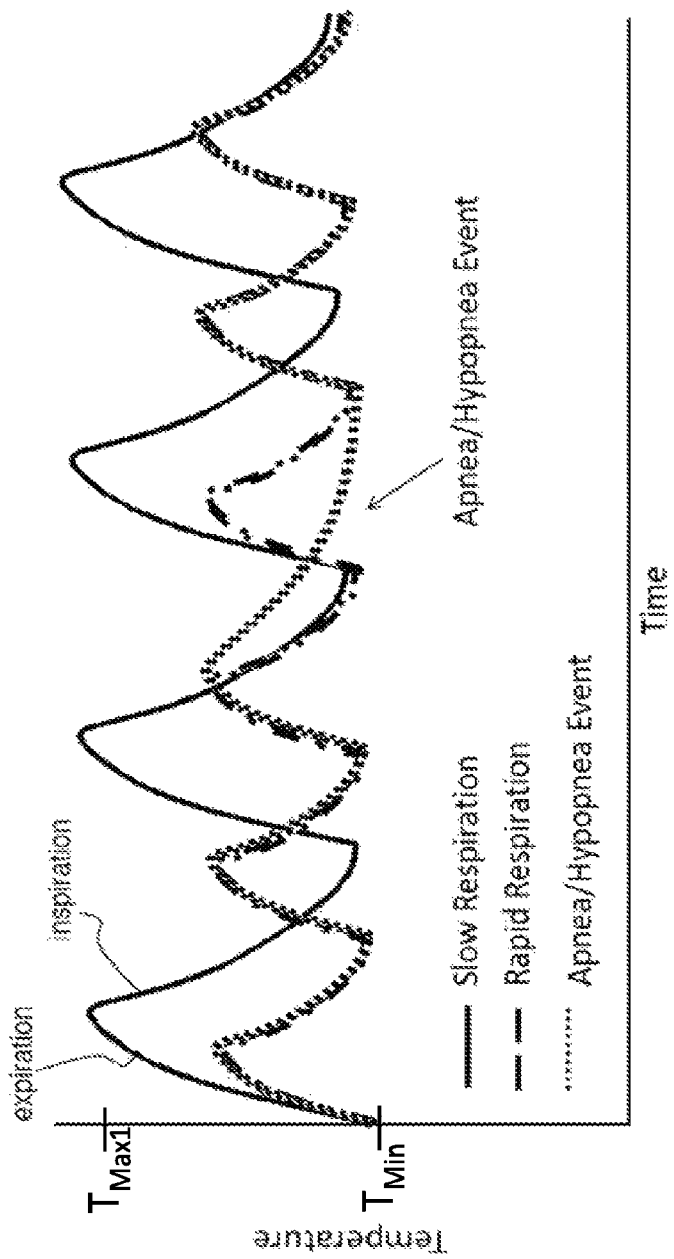
FIG. 1 is schematic plot illustrating temperature fluctuations acquired by a thermistor during respiration.

Some of these drawbacks of thermistors and thermocouples for assessing sleep disorders can be understood with reference to FIG. 1, which illustrates measurements of airflow temperature by a thermistor during respiration. Temperature measurements for three different respiratory conditions are illustrated, slow (normal) respiration, rapid respiration, and respiration during an apnea and/or hypopnea event. As shown, the measured temperature of respiratory airflow can differ between breathing in (inspiration or inhalation) and breathing out (expiration or exhalation). During inspiration, the temperature of air flowing across the thermistor can be relatively low because the air is drawn to the thermistor from the environment (e.g., at about room temperature). In contrast, during expiration, the temperature of air flowing across the thermistor can be higher because the expelled air is at about body core temperature. Thus, over a respiration cycle of inspiration and expiration, the temperature of respiratory airflow measured by the thermistor can rise from room temperature to body temperature during expiration and fall from body temperature to room temperature during inspiration.

Temperature measurements acquired by thermistors can be used to provide a binary indication of patient airflow, either breathing or not breathing. Thus, devices have been developed based upon thermistors to detect apnea (not breathing) relative to normal breathing, albeit with low sensitivity and specificity.

Notably, though, such measurements can result in a misleading pattern for assessment of airflow. As shown in FIG. 1, different maximum temperatures are measured by a thermistor during slow and rapid respiration. Notably the magnitude of temperature change measured during slow respiration is relatively a relatively large as compared to that measured during rapid respiration. This difference in the magnitude of measured temperature is as an artifact of the thermistor and not representative of actual differences in air temperature between slow and rapid respiration.

In general, sensors such as thermistors can require a certain amount of time, referred to as a time constant, for measurement of rapid temperature changes within their accuracy tolerance. When measuring air temperature during slow respiration, the temperature changes relatively lowly as compared to the thermistor time constant and can be substantially completely measured. In contrast, when measuring air temperature during rapid respiration, the temperature change is relatively fast compared to the thermistor time constant and thermistor can fail to respond quickly enough for complete measurement of the rise in temperature during expiration before cooling occurs during inhalation, even if the same airflow velocity is maintained in both cases.

For this reason, thermistors can fail to detect hypopneas, leading to significant numbers of false negatives. As discussed above, hypopnea can be characterized as reduced breathing by at least 30%, rather than cessation of breathing. With further reference to the respiration cycle including an apneic episode in FIG. 1, the temperature change during inspiration can be seen to be relatively gradual. This reflects cooling of the thermistor that occurs more slowly than during regular inspiration elsewhere in the plot. This gradual temperature change can occur due to reduced heat convection, since there can be little to no heat convection due to breathing during inspiration, when air temperature is expected to decrease. However, simply looking at the temperature-time plot of FIG. 1, it can be difficult or impossible to distinguish between apnea, hypopnea, or weak inspiration as the cause of the event.

Furthermore, while thermistors with short time constants can be used for better detection of apnea, such thermistors can remain insensitive to hypopneas or airflow limitations due to constricted airways and can fail to provide for their detection, again leading to more false negatives.

From the forgoing, it can be understood that existing thermistor-based systems for detecting airflow can be sufficiently insensitive to identify and/or distinguish hypopnea events from apnea events. This can lead to underreporting of hypopnea events and/or incorrect evaluation of the severity of sleep apnea, as characterized by the apnea-hypopnea index (AHI). Similarly, these devices can fail to detect and present flow limitations. Furthermore, existing devices employed for home-based sleep studies can share limitation similar to those of other clinical environments, namely requiring attachment of sensors to multiple locations on the patient's body. This can be both inconvenient and require professional attention.

Thus, there exists a continued need for improved systems for home-based assessment of sleep disorders, including apneas and hypopneas.

Accordingly, embodiments of the present disclosure can provide methods, systems, and devices for assessing respiration, apneas, hypopneas and other flow limitations using minimal energy and a single point device.

As discussed in greater detail below, embodiments of the present disclosure can provide systems utilizing a thermistor configured to measure heating and cooling cycles due to airflow from the patient's breathing cycle passing across the thermistor. Thermistor heating can occur during expiration, where the air can have a temperature of about body temperature (e.g., about 98.6° F. or about 37° C.), and thermistor cooling can occur during expiration, where the air can have a temperature of about room temperature (e.g., about 73° F. or about 23° C.).

In contrast to existing systems and methods, embodiments of the present disclosure can provide analysis of cooling during the breathing cycle (e.g., during inspiration), to determine airflow velocity across the thermistor for identification of sleep disorder events such as apnea, hypopnea, and other flow limitations, alone or in combination.

Thermistors have been used in certain configurations to measure fluid velocity using a self-heated thermistor similar to a hot-wire anemometer. This method is not suitable for battery operated small device. In certain embodiments, the intrinsic heating (also known as self-heating) can also be minimized by the use of relatively low current through the thermistor (e.g., about 0.01 mV to about 1 mV) when measuring its resistance. This configuration can allow the effects of perpetual intrinsic heating, generally seen with thermistors, to be disregarded. Additionally, this low current can provide extended battery life. However, in other embodiments, self-heating can be accounted for in the analysis.

Figure 2:
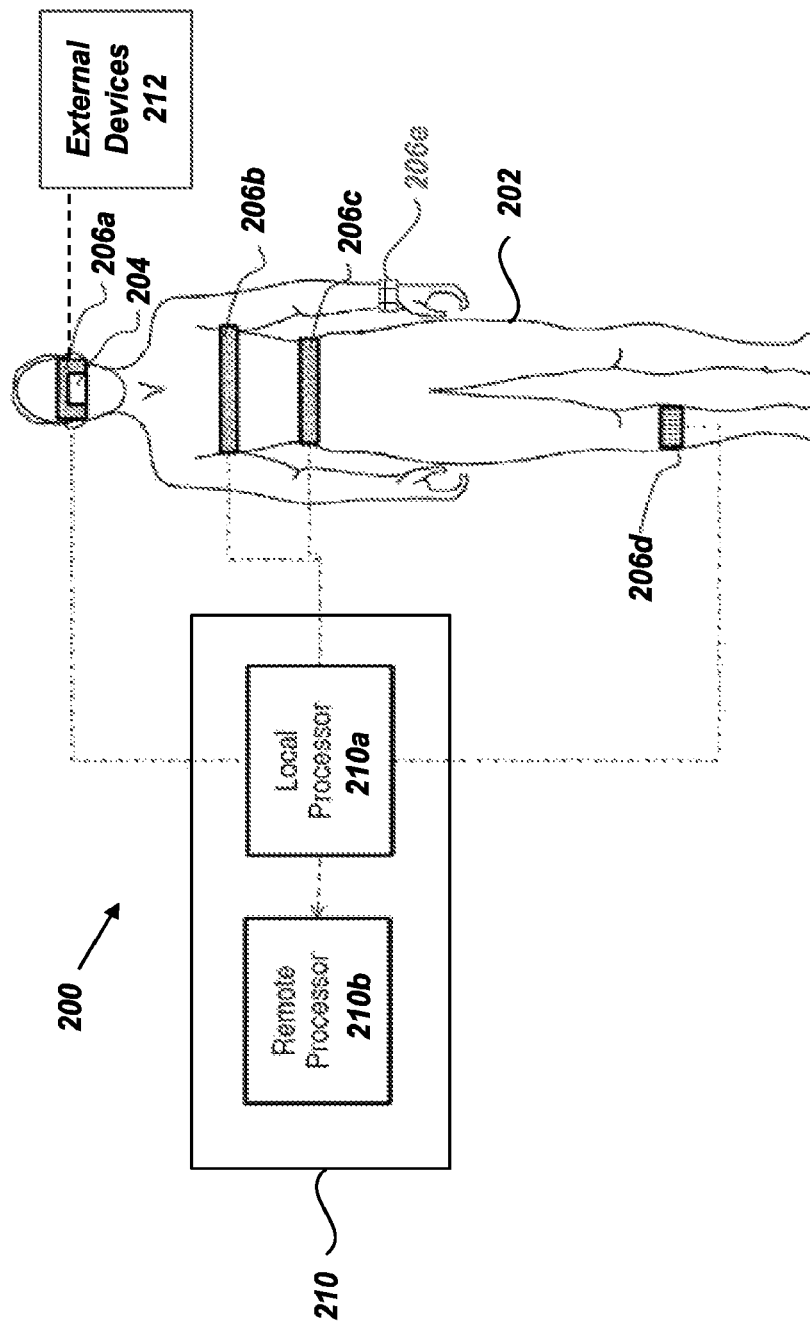
FIG. 2 is a schematic illustrating one exemplary embodiment of a sleep disorder assessment system including a wearable monitoring device.

FIG. 2 is a schematic illustration of one exemplary embodiment of a sleep disorder assessment system 200 for use with a human patient 202. The sleep disorder assessment system 200 can include a wearable monitoring device 204 configured to be coupled to the patient 202 for measurement of a variety of physiological parameters. As discussed in greater detail below, embodiments of the wearable monitoring device 204 can be configured to mount to a patient's nose for measurement of airflow, amongst other physiological parameters. Optionally, the sleep disorder assessment system 200 can also include one or more auxiliary monitoring devices 206 (e.g., 206a, 206b, 206c) configured for mounting to other portions of the patient's body and measuring other physiological parameters of the patient 202.

As described in greater detail below, the wearable monitoring device 204 can be a single point device devoid of wiring and having measurement accuracy comparable to instrumentation employed in sleep lab study. Embodiments of the wearable monitoring device 204, alone or in combination with the auxiliary monitoring devices 206 can be capable of obtaining all of the necessary parameters to determine the apnea-hypopnea index (AHI) and/or to abstract a hypnogram. Examples of physiological parameters can include one or more of oral airflow, nasal airflow, and blood oxygen saturation. However, a person skilled in the art will appreciate that embodiments of the wearable monitoring device 204 wearable monitoring device 204, alone or in combination with the auxiliary monitoring devices 206, can be configured to measure other parameters without limit.

As shown in FIG. 2, the sleep disorder assessment system 200 can also include a computing device 210 in communication with the wearable monitoring device 204 and the auxiliary monitoring devices 206. The computing device 210 can be configured to identify sleep disorders based upon analysis of the physiological parameters acquired by the wearable measurement device and/or auxiliary monitoring devices 206. The computing device 210 can adopt a variety of configurations. Examples can include, but are not limited to, server, computers, robots, cloud storage devices, health care provider servers, portable communication devices (e.g., cellular phones, tablet computing devices, etc.) and any combination thereof.

Embodiments of the sleep disorder assessment system 200 can also provide for performing a longitudinal sleep study so as to properly determine the apnea status of an individual over a period of time.

Embodiments of the wearable monitoring device 204 can also be configured to control one or more external devices 212. As an example, an external device 212 can include a Continuous Positive Airway Pressure therapy device ('CPAP') or the like devices associated with sleep disorders and/or oxygen saturation. Optionally, the sleep disorder assessment system 200 can include a flow sensor that may be employed to control the functionality of the external device 212. For example, the sleep disorder assessment system 200 can be configured to monitor and identify airflow during sleep may be utilized to control a CPAP device. In certain embodiments, the sleep disorder assessment system 200 can be configured to control the timing and volume of oxygen delivery to a user through a CPAP machine based upon identification of airflow during sleep.

First Wearable Monitoring Device Embodiment

An embodiment of the wearable monitoring device 204 in the form of a nasal clip 300 is illustrated in FIG. 3. As discussed in greater detail below, the nasal clip 300 can include a plurality of sensors configured for measuring physiological parameters of a patient associated with sleep disorders and electronic circuitry to facilitate operation and control of the plurality of sensors. The nasal clip 300 can also be configured to be comfortably worn by a patient during sleep without requiring complicated wiring, avoiding hindering of sleep and allowing for sleep in a natural setting.

Figure 3A:
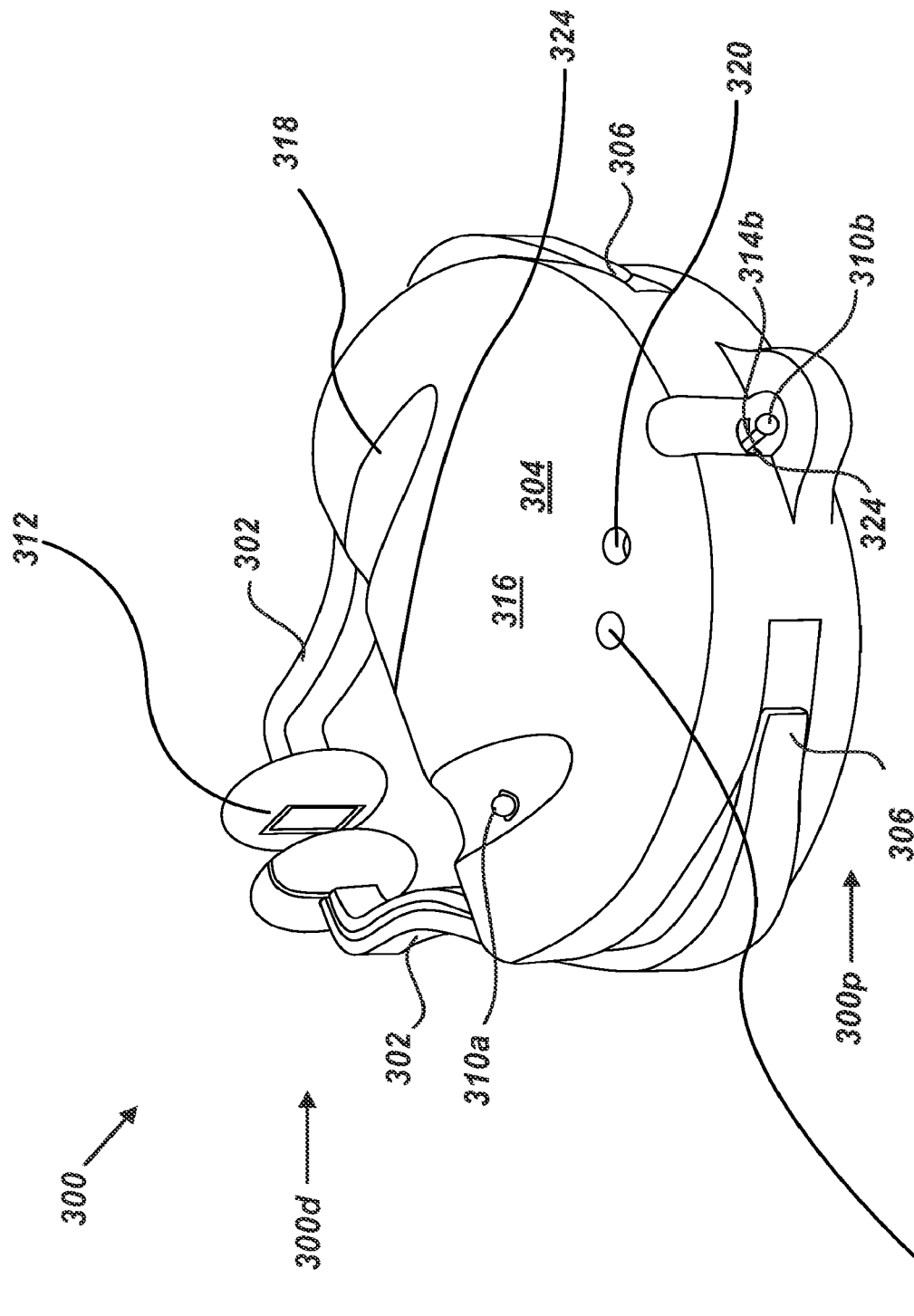
FIG. 3A is a rear perspective view of one exemplary embodiment of a wearable monitoring device of FIG. 2 including a nasal clip.
Figure 3B:
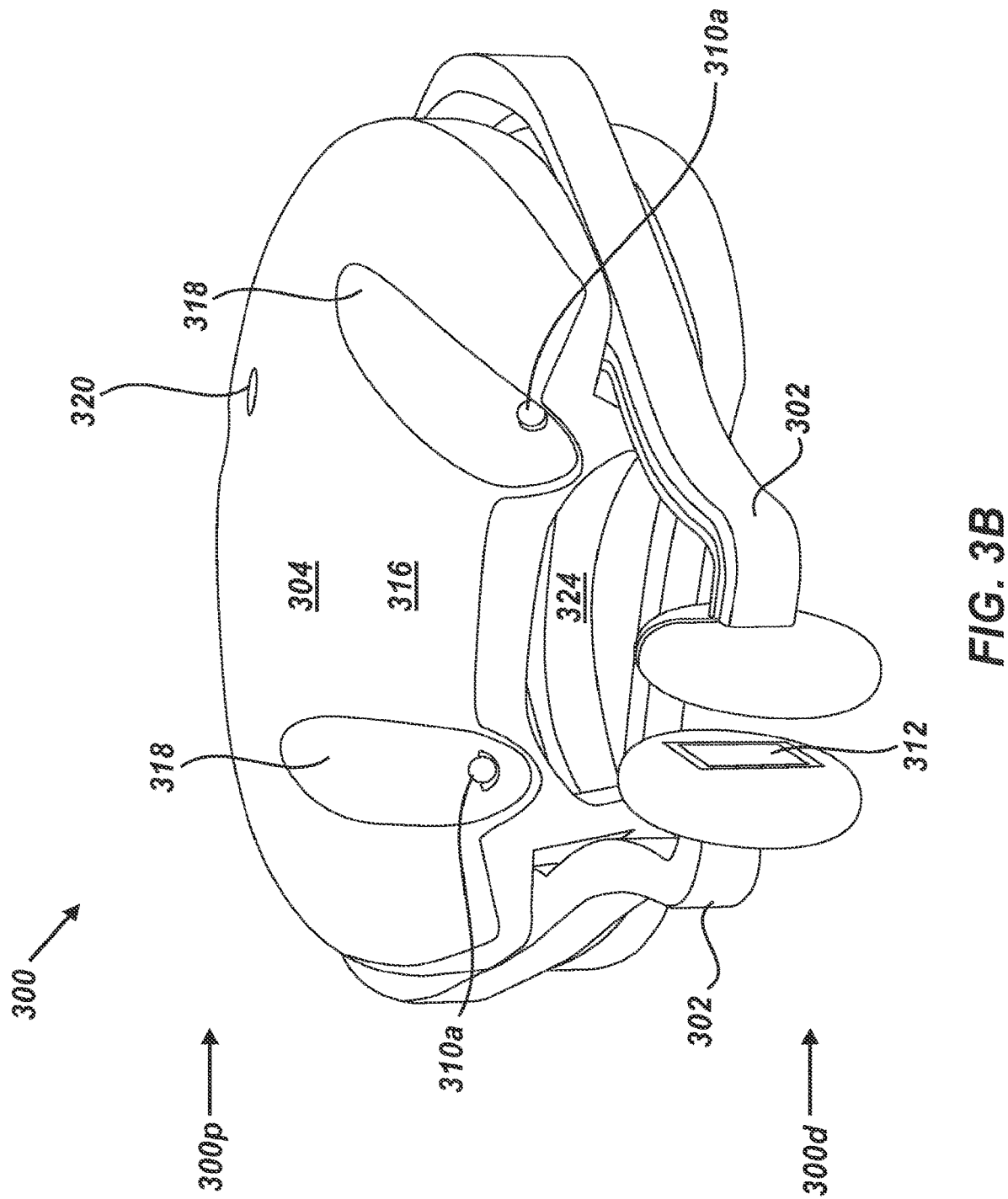
FIG. 3B is a front perspective view of one exemplary embodiment of a wearable monitoring device of FIG. 2 including a nasal clip.

As shown in FIGS. 3A-3B, the nasal clip 300 can extend between a distal end 300d and a proximal end 300p and it can include distal arms 302 and a body 304. The distal arms 302 can be generally elongated and they can extend distally outwards from the body 304. The distal arms 302 can be joined together and/or hinged to one or more hinge members 306 coupled to the body 304.

The hinge members 306 can be configured to allow the distal arms 302 to be coupled to human nostrils. As an example, the hinge members 306 can be configured to allow movement of one and/or both of the distal arms 302 to move with respect to one another. This movement can allow lateral separation of the distal arms 302 by a distance greater than a thickness human nasal septum. In an embodiment, this distance can be a minimum of about 0.75 mm and a maximum of about 3 mm That is, the hinge member 306 can allow at least one of the distal arms 302 to separate terminal ends of the distal arms 302 from one another by an amount sufficient to receive a nasal septum between the distal arms 302.

In additional embodiments, the hinge member 306 can also bias at least one of the distal arms 302 laterally towards the other. When the distal arms 302 are positioned within a human patient's nostrils, this bias can cause the distal arms 302 to engage the nasal septum and exert a compressive force upon the nasal septum sufficient to retain the nasal clip 300 coupled to the patient's nose without additional support. As an example, the compressive biasing force can be sufficient to retain the nasal clip 300 on the patient's nose under the force of gravity, alone or in combination with movement of the patient (e.g., movement during sleep). However, the compressive biasing force can be low enough such that the nasal clip 300 does not damage the nasal septum.

In an embodiment, one or more airflow sensors 310a can be mounted to the distal arms 302 and configured to determine nasal airflow 308a passing through the nostrils. As shown in FIGS. 3A-3B, the airflow sensors 310a can be positioned within one or more channels 318 extending along an outer surface of the body 304 along the distal arms 302 such that at least a portion of at least one of the airflow sensors 310a is in thermal communication with nasal airflow when the nasal clip 300 is coupled to the patient's nose. As also shown, each channel 318 can include an individual airflow sensor 310a configured to measure nasal airflow 308a from an adjacent nostril (e.g., left and right nostrils). However, in alternative embodiments (not shown), one or more channels and corresponding airflow sensors can be positioned within a distal arm. As discussed in greater detail below, embodiments of the airflow sensors 310a can be thermistors.

In another embodiment, the nasal clip 300 can include one or more pulse oximeter sensors 312 mounted to the distal arms 302. The pulse oximeter sensors 312 can include at least two light sources and a photosensor (not shown) for determining blood oxygen saturation from the vasculature of the nasal septum. In certain embodiments, the pulse oximeter sensors 312 can further determine the patient's heart rate. The pulse oximeter sensors 312 can be located on the distal arms 302 for positioning across the nasal septum, above the columella. As shown in FIGS. 3A-3B, each distal arm 302 can include a pulse oximeter sensor 312. However, in alternative embodiments (not shown), one or more pulse oximeter sensors can be coupled to a single distal arm.

Embodiments of the nasal clip 300 can also include at least one proximal arm 314 coupled to the body 304 and configured to measure oral airflow from the mouth. As shown in FIG. 3A, the proximal arm 314 can be generally elongated and extend proximally from the body 304. The proximal arm 314 can also include at least one airflow sensor 310b (e.g., a thermistor) for oral airflow measurement. The proximal arm 314 can be shaped and positioned such that, when the nasal clip 300 is coupled to the patient's nose (e.g., received between the distal arms 302), the body 304 can rest along the philtrum and the proximal arm 314 can be positioned in thermal communication with oral airflow 308a from the patient's mouth. That is, along the upper lip and optionally below the philtrum. The nasal clip 300 is illustrated in FIG. 3A as including one proximal arm 314. However, in alternative embodiments (not shown), the nasal clip can include two or more proximal arms, each including an airflow sensor so as to provide for additional oral airflow measurements.

The body 304 can also house electronic circuitry 316. The electronic circuitry 316 can be provided in electrical communication with the sensors 310a, 310b, 312. The electronic circuitry 316 can include one or more of processors, control modules, memory modules, and power modules, for controlling and operating the functions of physiological signal sensors associated with nasal clip 300 (e.g., 310a, 310b, 312).

In certain embodiments, the electronic circuitry 316 can provide for analysis of physiological data provided from sensors associated with the nasal clip 300 (e.g., 310a, 310b, 312) in order to assess a patient's the sleep disorder. As discussed in greater detail below, patient's sleep disorder may be identified by abstracting a hypnogram and/or assessing the patient's apnea-hypopnea index score from the physiological parameters acquired provided by the sensors 310a, 310b, 312.

In certain embodiments, the electronic circuitry 316 can include a display and/or indicator for displaying results and/or indicating function and/or status to an operator. The display can be provided in optional forms for example including but not limited to a LED indicator, multicolor LED indicator, alphanumeric display, LED display array, dot LED display array, LCD display, any combination thereof or the like.

In additional embodiments, the electronic circuitry 316 can include user interfaces allowing an operator to provide input to the nasal clip 300. Examples of user interfaces can include, but are not limited to, switches, buttons, touch pads, piezoelectric pads, and any combination thereof.

In further embodiments, the electronic circuitry 316 can include communication devices allowing communication between the nasal clip 300 with external computing devices (e.g., computing device 210), robots, and the like for transmission of physiological data acquired by the nasal clip 300. The communication devices can be configured to communicate via any communications protocol or medium, including but not limited to wired or wireless communication. Examples of wireless communication can include any of Wi-Fi, Bluetooth, optical communication, IR communication, cellular communication, and the like. Examples of wired communication can include, but are not limited to, USB interfaces, firewire interfaces, Ethernet communication, fixed line telephone communications (e.g., RJ10), etc.

In an embodiment, the airflow sensors 310a, 310b can be thermistors. As discussed above, devices employing thermistors for measurement of airflow temperatures and corresponding determination of sleep disorders have been problematic. However, embodiments of the preset disclosure provide novel thermal models that allow estimation of air velocity using thermistor-based temperature measurement which avoid these problems. Notably, these models can employ measurements of the rate of change of airflow temperature for determination of the airflow velocity.

Accordingly, to facilitate measurement of the rate of change of airflow temperature, embodiments of the disclosed systems can include thermistors configured to not to reach thermal equilibrium and/or steady state during at least one of an inhalation and/or exhalation period of a patient. As an example, if a thermistor reaches steady state and fully equilibrates with the temperature of nasal or oral airflow, the time derivative of the temperature can be approximately zero and the model can fail to accurately estimate the nasal or oral airflow velocity. In order to inhibit the thermistor from reaching thermal equilibrium/steady state during the respiration cycle, the thermistor can be provided with a time constant above a certain value. Furthermore, as discussed above, the time constant can be small enough to measure changes in respiratory airflow temperature during rapid breathing. Thus, the time constant of the thermistor can be provided within a selected range. The range of time constants can also be selected according to one or more characteristics of a patient, including but not limited to, age, sex, weight, nasal anatomy, oral anatomy, breathing cycle time, average inhalation period, average exhalation period, and any combination thereof. In certain embodiments, the thermistors can have a time constant greater than about 3 seconds. In further embodiments, the thermistors can have a time constant selected from the range between about 3 seconds to about 10 seconds. In additional embodiments, the thermistors can have a time constant greater than 10 seconds.

In further embodiments, the thermistors can be configured to operate using relatively little current. As an example, the thermistors can be configured to operation using about 0.01 mA to about 1 mA current. In this manner, self-heating of the thermistor during use can be substantially negligible compared to temperatures measured by the thermistor.

As discussed in greater detail below, airflow velocity along a selected airflow path (e.g., nasal or oral) can be determined by positioning the thermistor in the selected airflow path. So positioned, the thermistor can be allowed to heat from expired air at body temperature and cooled from inspirated air at room temperature. Cooling of the thermistor during inspiration along the same airflow path can be monitored in order to determine the airflow velocity within the selected airflow path. Airflow velocity can be determined based on the rate of temperature change of the thermistor and the temperature difference between inspirated and expirated air during inhalation. As an example, in one aspect, the conductance of heat flow between the thermistor's mass and the airflow can be used to measure airflow. In another aspect, the temperature dynamics during cooling of the thermistor can be analyzed.

In certain aspects, external surfaces of the nasal clip 300 that contact patient tissue (e.g., the distal arms 302) can be formed from biocompatible materials and/or coatings. These materials and/or coatings can ensure that the nasal clip 300 does not irritate, injure, or inflict pain on tissue of the nasal septum or any other anatomy that it is associated with. Examples of such materials and coatings can include, but are not limited to, silicones.

In other aspects, the nasal clip 300 can be associated with additional nasal structures. Examples of such nasal structures can include, but are not limited to, one or both ala.

In alternative embodiments, the wearable monitoring device can be associated over other facial structures for example including but not limited to the ears, chin, neck, nape, facial structure, mouth, forehead, any combination thereof or the like anatomical structure suitable for securely coupling the wearable monitoring device with the patient.

The nasal clip 300 can include additional sensors to facilitate sleep disorder assessment, monitoring, and/or analysis. In general, the additional sensors can be positioned anywhere on or within the nasal clip 300. Example positions can include, but are not limited to, on or within the body 304 and on or within the distal arms 302 or the proximal arm 314.

In one embodiment, the additional sensors can include one or more audio sensors 320 (e.g., microphones). The audio sensors 320 can provide for recording and/or analyzing sound associated with sleep disorders for example including but not limited to snoring. In certain embodiments, the audio sensors 320 can be configured to detect sleep talking, somniloquy, or the like.

In certain embodiments, audio sensors 320 can be configured to automatically filter sounds associated with snoring and/or the frequency of snoring that are known to be associated with sleep disorders such as apnea. Optionally a filter having a threshold frequency of about 800 Hz can be utilized. Optionally the filter can be a low pass filter, band pass filter, a high pass filter, or any combination thereof.

In certain embodiments, the additional sensors can include one or more accelerometers 322. The accelerometers 322 can be configured for detection of movement, position, inclination, and/or orientation of a patient's body (e.g., head, torso) as a function of time in three dimensions during sleep when mounted to the patient's nose. Examples of accelerometers 322 can include, but are not limited to, three axis accelerometers, gyroscope sensors, motion sensors, and any combination thereof.

Data acquired by the accelerometers 322 can be analyzed to determine breathing effort. In other embodiments, data acquired by accelerometers 322 can be employed for determining the sleeping position and/or inclination of a patient. That is, the accelerometers 322 can be utilized as an inclinometer. Optionally, this data from the accelerometer 322 can be communicated to the computing device 210 for determination of a patient's apnea-hypopnea index (AHI).

In certain embodiments, the additional sensors can include one or more pressure sensors 324. As shown in FIGS. 3A-3B, the pressure sensors 324 can be configured to measure one or more parameters such as resistance to flow, oral airflow, nasal airflow, and any combination thereof. The pressure sensors 324 can be located within the nasal clip 300 (e.g., a distal end of the body) for location adjacent to the nostrils when mounted to the patient's nose. The pressure sensors 324 can include an air intake in a bowl-like shape in fluid communication with a pressure sensing element within the body 304 (not shown). In alternative embodiments (not shown), the pressure sensors can be provided in the form of a cannula protruding into the nostrils and in fluid communication with the pressure sensing elements.

Second Wearable Monitoring Device Embodiment

Figure 4B:
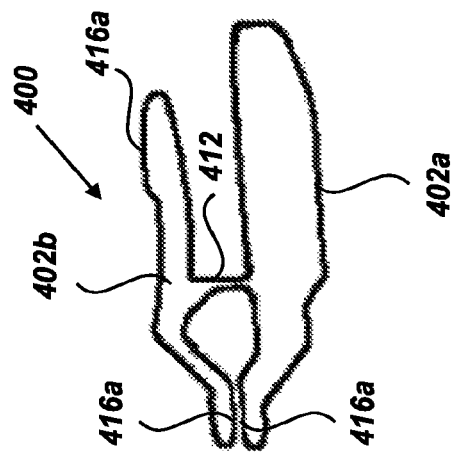
FIG. 4B is a side view of the two piece nasal clip of FIG. 4A.
Figure 4A:
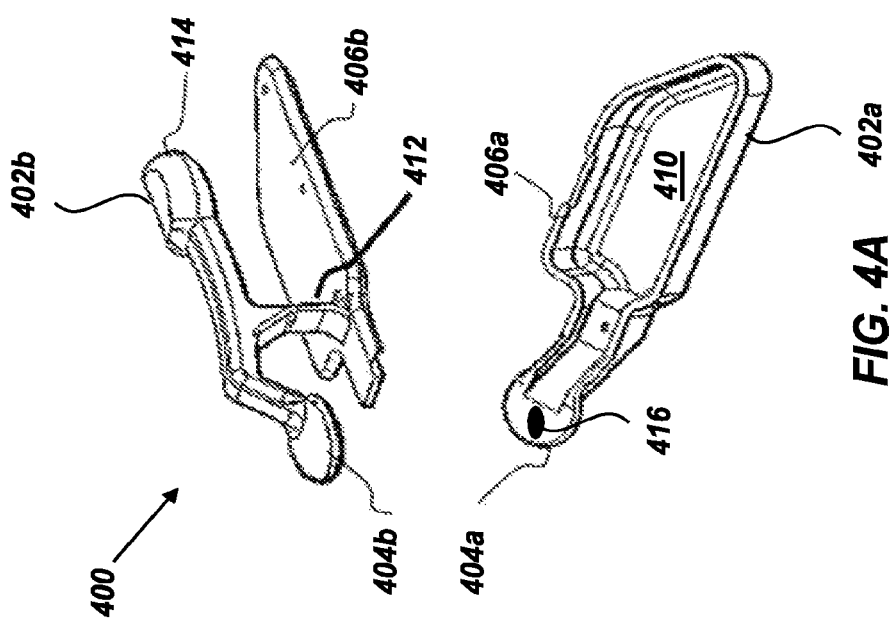
FIG. 4A is an exploded perspective view of another exemplary embodiment of a wearable monitoring device of FIG. 2 including a two piece nasal clip.

FIGS. 4A-4B illustrate another exemplary embodiment of the wearable monitoring device 204 in the form of a split nasal clip 400. The split nasal clip 400 can be employed similarly to the nasal clip 300 for measurement of physiological parameters of the patient but can be divided into two parts, a first portion 402a and a second portion 402b. FIG. 4A shows the split nasal clip 400 in an exploded side view while FIG. 4B shows the split nasal clip 400 in an assembled side view.

The first portion 402a can include a first distal arm 404a and a first body portion 406a. The first body portion 406a can define a cavity 410 for receiving and fitting electronic circuitry (e.g., electronic circuitry 316; not shown). The second portion 402b can include a second distal arm 404b, a second body portion 406b, a hinge member 412, and a proximal arm 414.

The second portion 402b can be shaped as a cover configured for coupling to the first portion 402a. As an example, the second portion 402b can form a snap-fit or friction fit with the first portion 402a. In alternative embodiments, the first and second portions 402a, 402h can be secured to one another by other mechanisms, such as hooks, threaded fasteners, welds, adhesives, and the like.

Sensors 416 can be mounted to one or both the first and second distal arms 404a, 404b and the proximal arm 414 and coupled to electronics housed within the cavity 410 for measurement of nasal airflow, oral airflow, blood oxygen saturation, and/or other physiological parameters, as discussed above. In an embodiment, one or more of the sensors 416 can be an airflow sensor (e.g., 310*a*) mounted to the first and second distal arms 404*a*, 404*b* and configured to measure nasal airflow from the nostril in which its distal arm 404*a*, 404*b* is positioned. In another embodiment, one or more of the sensors 416 can be a pulse oximeter sensor (e.g., 312) mounted to the first and second distal arms 404*a*, 404*b* for measurement of oxygen saturation and/or patient heart rate. In a further embodiment, one or more of the sensors 416 can be an airflow sensor (e.g., 310*b*) mounted to the proximal arm 414 and configured for measurement of oral airflow.

The split nasal clip 400 can be deployed similarly to the nasal clip 300. As an example, the hinge member 412 can bias the second distal arm 404*b* towards the first distal arm 404*a*. As a result, the first and second distal arms 404*a*, 404*b* are positioned within a patient's nostrils, they can exert a compressive force upon the nasal septum sufficient to retain the split nasal clip 400 coupled to the patient's nose without support. So positioned, the sensors 416 (e.g., airflow sensors 310*a*) can be positioned along the first and/or second distal arms 304*a*, 304*b* such that at least a portion of at least one of the sensors 416 can be positioned within a patient's nostril when the split nasal clip 400 is coupled to the patient's nose. Similarly, when the nasal clip 300 is coupled to the patient's nose, the body 314 can rest along the philtrum and the proximal arm 414 can be located along the upper lip (e.g., optionally below the philtrum) and within an oral airflow pathway for measurement of oral airflow.

Third Wearable Monitoring Device Embodiment

Figure 5A:
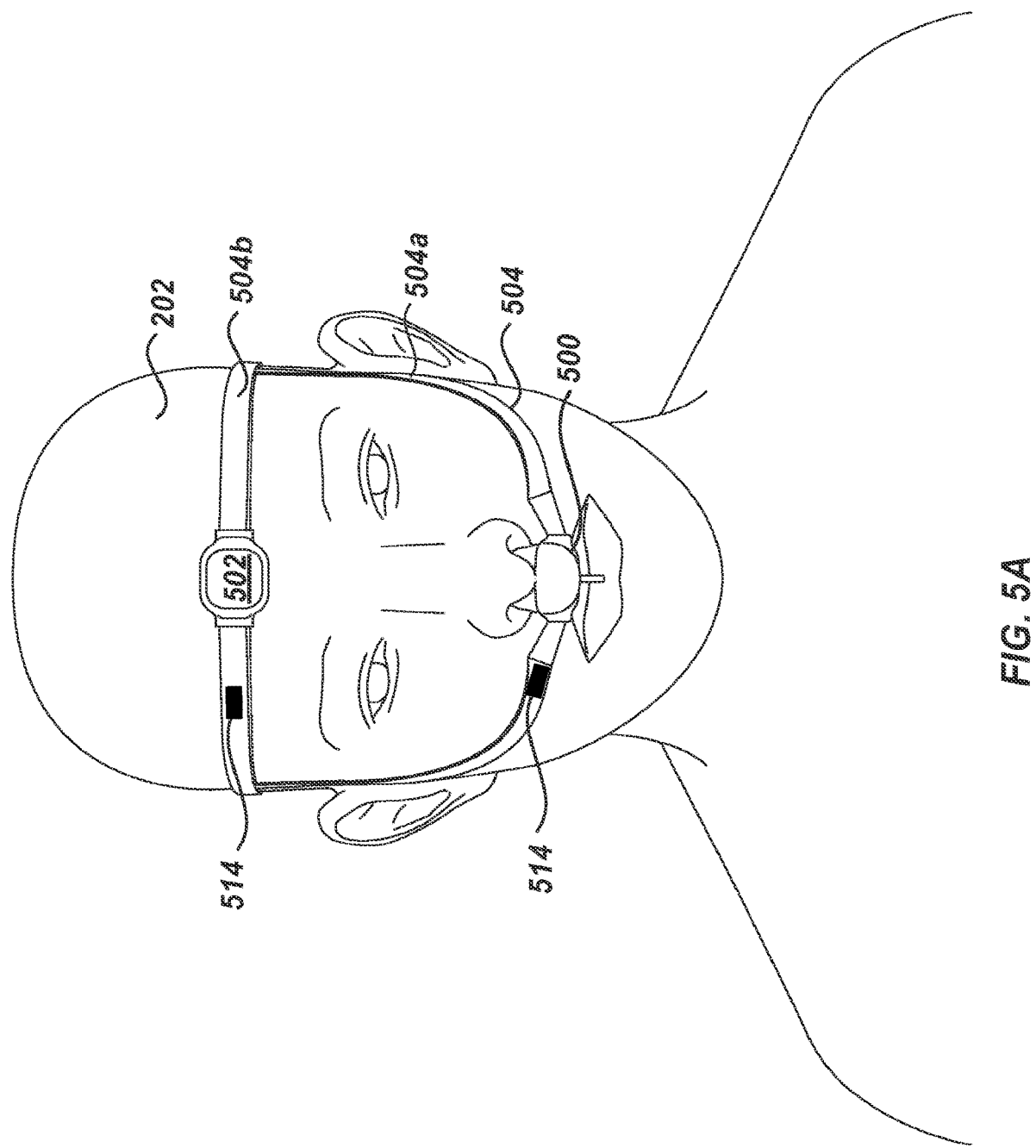
FIG. 5A is a front view of another exemplary embodiment of a wearable monitoring device of FIG. 2 including an airflow monitoring device and an auxiliary monitoring device mounted to a patient by a band.
Figure 5B:
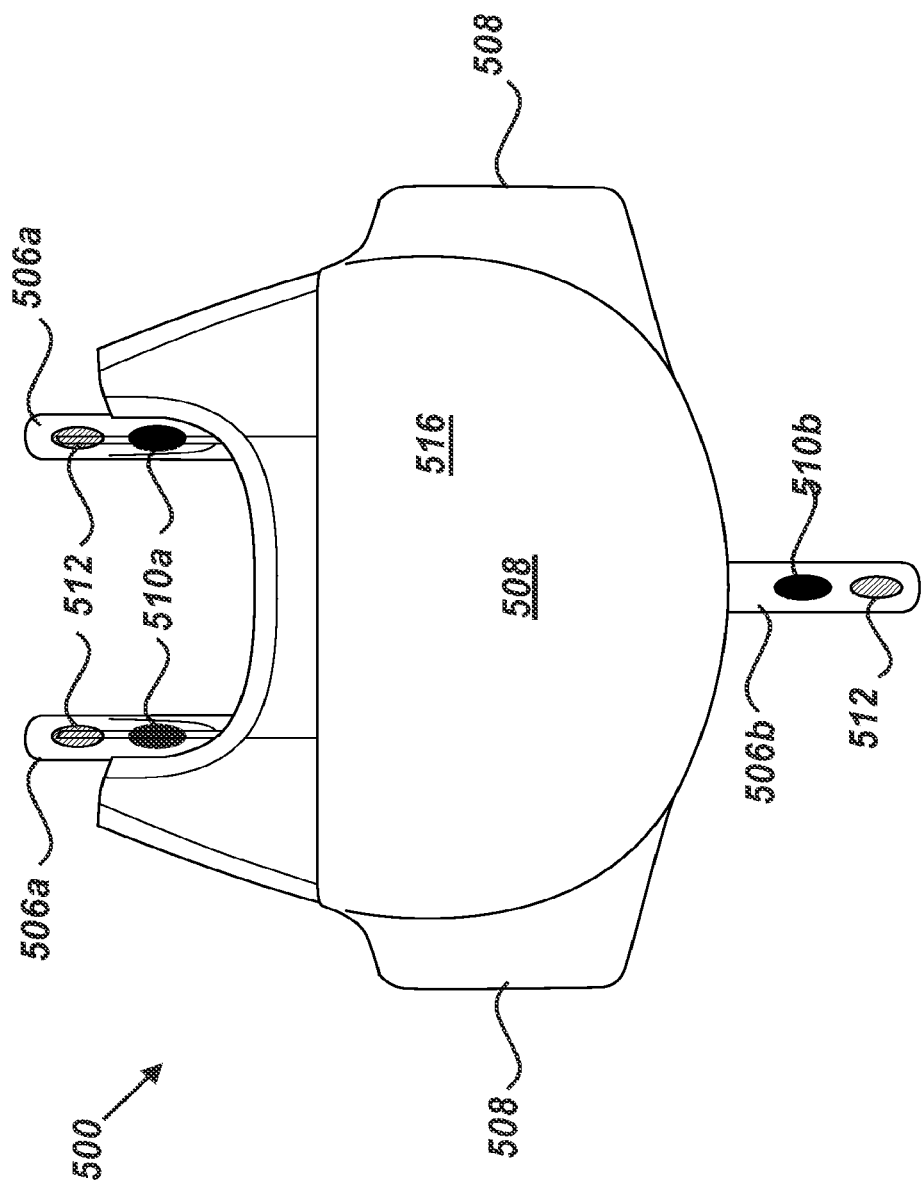
FIG. 5B is an expanded detail view of the airflow monitoring device of FIG. 5A.
Figure 5C:
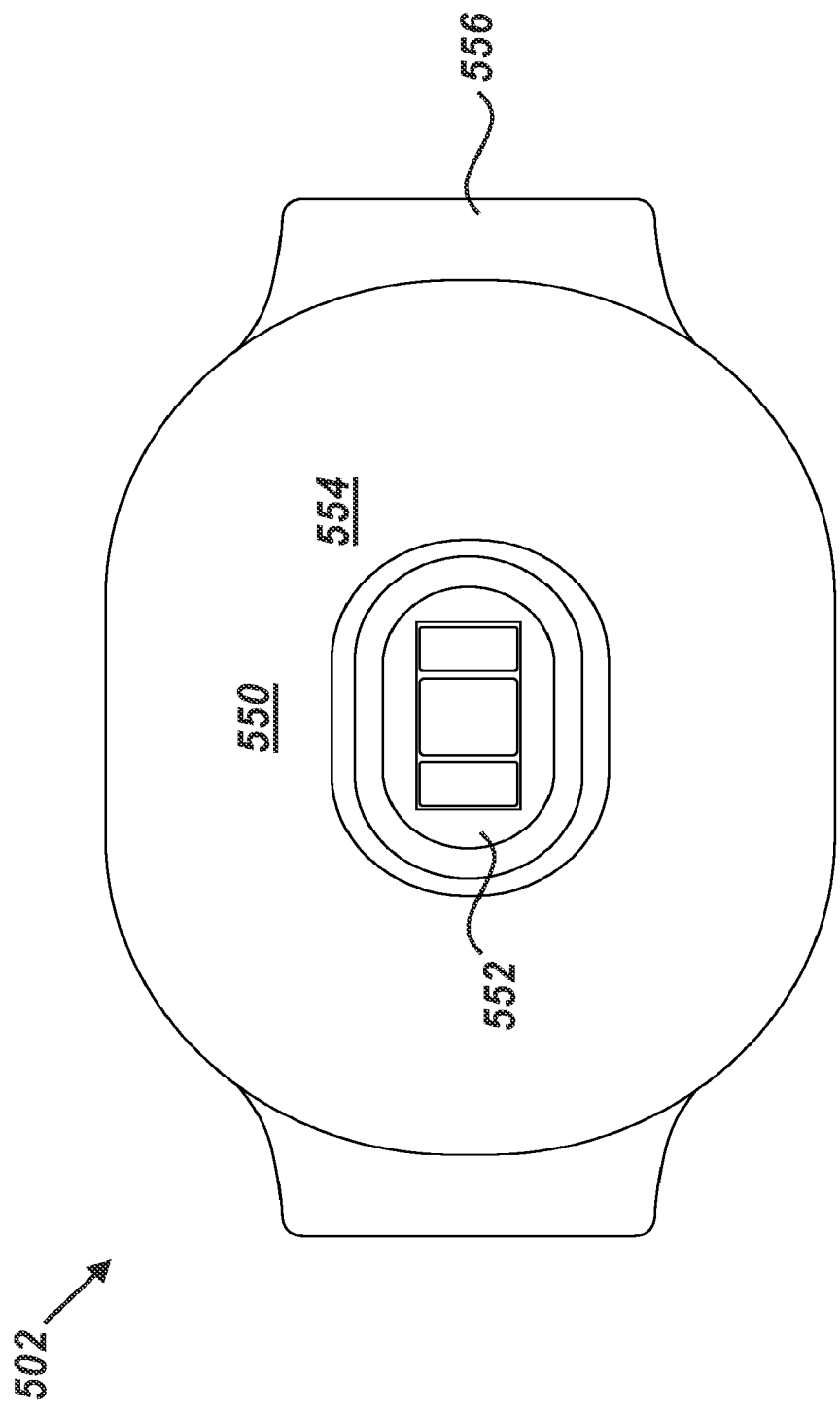
FIG. 5C is an expanded detail view of one exemplary embodiment of an auxiliary monitoring device of FIG. 5A.

FIGS. 5A-5C illustrate another exemplary embodiment of the wearable monitoring device 204 in the form of an airflow monitoring device 500 and one or more auxiliary sensors 502, each separate from the other. As discussed in greater detail below, the airflow monitoring device 500 can be similar to the nasal clip 300 and it can be configured for measurement of physiological parameters of the patient 202. However, rather than supporting itself when attached to the patient 202, the airflow monitoring device 500 can be configured for support by the band 504 (e.g., along opposed lateral edges 508). As shown in FIG. 5A, the hand 504 can include a first portion 504*a* that extends under the patient's nose and is coupled to the airflow monitoring device 500 and a second portion 504*b* that extends about the patient's head and is coupled to the auxiliary sensors 502. The band 504 can be formed from an elastically deformable material (e.g., an elastomer), allowing it to adapt to the shape of a human head for frictional engagement.

The airflow monitoring device 500 is shown in greater detail in FIG. 5B. Similar to the nasal clip 300, the airflow monitoring device 500 can include one or more distal arms 506*a* and at least one proximal arm 506*b* coupled to a body 508. The distal arms 506*a* can be offset from one another by a distance sufficient to allow a human nasal septum to be positioned therebetween. Sensors 510*a*, 510*b* and pulse oximeter sensors 512 can be mounted to one or both the distal arms 502*a* and the proximal arm 502*b*. In this configuration, when the nasal septum is received between the distal arms 506*a* and the body 508 is engaged with the band 504, a terminal end of each of the distal arms 506 can be located within respective nostrils adjacent to the nasal septum and the sensors 510*a* can be in thermal communication with nasal airflow.

The sensing elements 510*a*, 510*b*, 512 can be provided in electrical communication with the power source 514 and electronic circuitry 516 for receiving electrical power, receipt of commands, and transmission of acquired physiological parameters. In certain embodiments, at least one of the electronic circuitry 516 and the power source can be positioned within the band 504. In other embodiments (not shown), both the electronics and the battery can be positioned within the band, with the sensors being part of the airflow monitoring device.

As discussed above, the sensors 510*a*, 510*b* can be thermistors configured for measurement of nasal and/or oral airflow. The thermistors of sensors 510*a*, 510*b* can be similar to those discussed above regarding sensors 310*a*, 310*b*. Similarly, the sensors 512 can be pulse oximeter sensors configured to measure oxygen saturation and/or patient heart rate, similar to those discussed above regarding sensors 312.

The sensors 510*a* can be positioned along the distal arms 506*a* such that at least a portion of at least one of the sensors 510*a* is positioned within the patient's nostril when the airflow monitoring device 500 is coupled to the patient's nose. As shown in FIGS. 5A-5B, each distal arm 506*a* can include an individual sensor 510*a* configured to measure nasal airflow from the nostril in which its distal arm 506 is positioned. However, in alternative embodiments (not shown), one or more airflow sensors can be coupled to a single distal arm, rather than both.

The proximal arm 506*b* can be shaped and positioned such that, when the airflow monitoring device 500 is coupled to the patient's nose by the band 504, the body 508 can rest along the philtrum and the proximal arm 506*h* can be located along the upper lip (e.g., optionally below the philtrum). The airflow monitoring device 500 is illustrated in FIGS. 5A-5B as including one proximal arm 506*b*. However, in alternative embodiments (not shown), the airflow monitoring device can include two or more proximal arms, each including an airflow sensor so as to provide for additional oral airflow measurements.

FIG. 5C illustrates an embodiment of the auxiliary sensors 502. The auxiliary sensors 502 can include a body 550 housing one or more sensing elements 552 therein. The sensing elements 552 can be in electrical communication with the power source and electronic circuitry 554 for receiving electrical power, receipt of commands, and transmission of acquired physiological parameters. As shown, lateral edges 556 of the auxiliary sensors 502 can be configured to couple with the band 504 for mounting to a patient's head so that the sensing elements 552 can be positioned proximate to or in contact with the patient's skin.

In certain embodiments, the auxiliary sensors 502 can replace or duplicate the functionality of sensors mounted to the airflow monitoring device 500. As an example, the auxiliary sensors 502 can include a pulse oximeter sensor similar to sensor 512. Accordingly, in some embodiments, the sensor 512 can be omitted from the airflow monitoring device. Other embodiments of the auxiliary sensors 502 can include, but are not limited to, temperature sensing devices (e.g., thermistors, thermocouples, etc.), audio recording devices (e.g., microphones), motion detection devices configured for detection of movement, position and/or orientation of a patient during sleep (e.g., accelerometers, gyroscopes, motion sensors, and any combination thereof), as discussed above.

Single and Multiple Use Configurations

Each of the devices 300, 400, 500, 502 can be independently configured for single use or multiple uses. Single use devices can be disposed of upon completion of a single sleep study. In contrast, devices configured for multiple uses can include one or more components designed to be reused. Optionally, devices configured for multiple uses can also include one or more components designed to be disposed of after a single use. For example, the body of the devices 300, 400, 500, 502 (e.g., 304, 406a, 406h, 508, 550) and hinge members 306, 412, can be provided in a multi-use portion that may be used multiple times while other portions that couple with the user's nostrils, for example distal and proximal arms (e.g., 302a, 302b, 414, 506a, 506h) can be disposable and replaceable after use.

Computing Devices

In certain embodiments, the computing device 210 can be in wireless communication with the wearable monitoring device 204 and can be configured to analyze physiological parameters acquired by the wearable monitoring device 204 and/or auxiliary monitoring devices 206 in order to determine and/or assess sleep disorders of the patient 202.

With further reference to FIG. 2, embodiments of the computing device 210 can include a remote computing device 210a. The computing device 210 can be a server computer, robot, cloud storage device, health care provider server, mobile communication device or the like device having processing and communication capabilities running software and/or hardware adapted to analyze physiological parameters acquired by the wearable monitoring device 204. In certain embodiments, the computing device 210 can be realized in the form of a network of computers and/or processing devices and/or robots.

In other embodiments, the computing device 210 can be provided in the form of one or more individual computers and/or robots that function together to process and/or analyze physiological parameters acquired by the wearable monitoring device 204. Each computing device and/or robot can be configured to provide a specific analysis with respect to at least one set of physiological parameters and/or other data acquired by the wearable monitoring device 204. As an example, a first computer forming a part of the computing device 210 can be utilized to analyze pulse oximeter data; a second computer forming another part of the computing device 210 can be utilized to analyze nasal airflow data; and a third computer forming another part of the computing device 210 can be utilized to analyze oral airflow data.

In other embodiments, the computing device 210 can include a remote computing device 210a and a local computing device 210b. As an example, the wearable monitoring device 204 can be in direct communication with the local computing device 210b which in turn can communicate with the remote computing device 210a. In this configuration, the local computing device 210b can be configured to analyze physiological parameters acquired by the wearable monitoring device 204.

In this embodiment, the wearable computing device 204 can be configured with minimal electronic circuitry necessary to acquire and transmit physiological parameters to the local computing device. That is, the wearable computing device can acquire physiological parameters of a patient suitable for rendering a sleep disorder assessment without analyzing the acquired physiological parameters. Instead, the local computing device 210b can be configured to analyze the acquired physiological parameters. As an example, in the context of devices 300, 400, 500, the electronic circuitry 320, 514 employed for analysis of acquired physiological parameters can be omitted.

In certain embodiments, the local computing device 204b can be a portable computing device, such as a smartphone or tablet computing device, executing a dedicated application for analyzing physiological parameters measured by the wearable computing device (e.g., 204, 300, 400, 500). In other embodiments, the local computing device 204b can be a dedicated device running a dedicated application and/or the like software provided for processing data directly provided from the wearable computing device (e.g., 204, 300, 400, 500).

In additional embodiments, the local computing device 204b can be configured to provide an initial analysis of physiological parameters acquired by the wearable monitoring device for sleep disorder assessment. The remote computing device 204a, can be in communication with the local computing device 204b and it can be configured to provide higher processing functions that offer a more complete and/or thorough analysis of sleep disorders that cannot be performed (or cannot be performed in a selected time period) with the local computing device 204b and/or the wearable monitoring device (e.g., 204, 300, 400, 500).

Auxiliary Monitoring Devices

Optionally, embodiments of the sleep disorder assessment system 200 can also include one or more additional auxiliary monitoring devices 206, separate from any airflow monitoring devices (e.g., 204, 300, 400, 500) and configured for measuring additional physiological parameters. These additional physiological parameters can include, but are not limited to, electrooculography (EOG), electroencephalography (EEG), electromyography (EMG), respiratory effort, blood oxygen saturation, heart rate, and any combination thereof.

In one embodiment, the sleep disorder assessment system 200 can include an auxiliary monitoring device 206 in the form of a facial mask 206a. The facial mask 206a can be configured to acquire EOG measurements and transmit signals representing the EOG measurements to the computing device 210.

In another embodiment, the sleep disorder assessment system 200 can include an auxiliary monitoring device 206 in the form of chest belt 206b and/or abdominal belt 206c. The chest belt 206b and abdominal belt 206c can be configured to acquire respiratory effort measurements and to transmit signals representing the respiratory effort measurements to the computing device 210. The belts 206b, 206c can be provided in the form of devices that are capable of measuring respiratory muscle movements, chest movements, and/or abdominal movement suitable for determining respiratory effort. Examples of such devices can include, but are not limited to, resistive belts, piezo-resistive belts, and strain gages.

In a further embodiment the sleep disorder assessment system 200 can include an auxiliary monitoring device 206 in the form of EMG sensor and/or electrode array 206d. The EMG sensor/electrode array 206d can be configured to acquire EMG measurements and to transmit signals representing the EMG measurements to the computing device 210. The EMG sensor/electrode array 206d can be configured for use with one or more anatomical extremity. Examples of extremities can include but are not limited to, legs, arms, hands, fingers, toes, or other anatomy having a musculature of interest. In certain embodiments, the EMG sensor/electrode array 206d can be configured to engage (e.g., wrap around) a lower leg extremity. In this manner, EMG measurements of the leg can be acquired for depicting leg movement activity during sleep, which can provide for further sleep disorder analysis.

In an additional embodiment, the sleep disorder assessment system can include an auxiliary monitoring device 206 in the form of a pulse oximeter sensor 206e. The pulse oximeter sensor 206d can be similar to pulse oximeter sensors 312, and it can be configured to acquire blood oxygen saturation and/or patient heart rate and to transmit signals representing the blood oxygen saturation and/or patient heart rate to the computing device 210. The pulse oximeter sensor 206e can be configured for use with any portion of the patient's anatomy. Examples can include, but are not limited to, the wrist, as shown in FIG. 2, the head, as shown in FIG. 5A (e.g., auxiliary sensor 502), the ankle, etc.

Analysis of Thermistor Cooling for Airflow Measurement

Instead of measuring temperature using simply the thermistors resistance, embodiments of the disclosed airflow sensors can be employed to estimate actual fluid velocity from measurements of nasal and/or oral airflow. The velocity of airflow passing across a thermistor v can be determined from an analysis of its thermal behavior when cooling or heating depending whether room temperature and/or body temperature are known. In an example, the room temperature can be easily measured and, therefore we use of the cooling phase is discussed in detail below.

The cooling rate of a thermistor can be related to the change in thermal energy of the thermistor. The thermal energy stored in a thermistor can be expressed by Equation 1:

$$E = MC_o T \quad (1)$$

Where T is the thermistor temperature, M is the mass of the thermistor, and $C_o$ is the specific heat of the thermistor at temperature T. The rate of heat flow q into the thermistor's mass can be given by Equation 2:

$$q = C_T \dot{T} \quad (2)$$

where $C_T$ is the heat capacity of the thermistor's body mass ($MC_o$) and $\dot{T}$ is the rate of change of temperature of the thermistor.

The rate of heat flow q can also be described as a function of a difference between a temperature of inhaled air $T_A$ and the thermistor's temperature T and the airflow velocity v. Assuming heat transfer between air and the thermistor's body mass, q in Equation 2 can be replaced by $$\frac{1}{R(v)}(T_A - T)$$

to yield Equation 3:

$$\frac{1}{R(v)}(T_A - T) = C_T \dot{T} \quad (3)$$

where R(v) is the total heat resistance between the thermistor and the air and is a function of airflow velocity V. $C_T$ is a constant and generally can be provided by the thermistor manufacturer, while T and $\dot{T}$ are measured by the thermistor. $T_A$ can be acquired by independent measurement of air temperature in the environment surrounding the patient. Accordingly, Equation 3 can allow determination of heat resistance R(v) by experiment based upon measurements of T and $\dot{T}$.

One approach to experimentally determining R(v) can employ a functional relationship between heat resistance R(v) and airflow velocity v, given below in Equation 4 based on King's equation that is used for hot wire anemometry:

$$R(v) = \frac{1}{a + bv^c} \quad (4)$$

where a, b, and c are constants associated with the thermistor and can be determined. As an example, these constants can be determined experimentally by a controlled experiment where airflow velocity v is a controlled and measured variable (e.g., using an air flowmeter).

Once the constants a, b, and c are known, airflow velocity v can be determined by substituting heat resistance R(v) of Equation 4 into Equation 3 and solving for airflow velocity v, yielding Equation 5:

$$v = \sqrt[c]{\frac{1}{b}\left(\frac{-C_T \dot{T}}{(T - T_A)} - a\right)} \quad (5)$$

Another approach for determining air velocity v can utilize Equation 3, rewritten below as Equation 3' to place all measured temperature quantities on one side:

$$G(v) = \frac{1}{R(v)C_T} = \frac{\dot{T}}{(T_A - T)} \quad (3')$$

G(v) can be measured experimentally and a curve fitting technique can be used to obtain a relation between G(v) and airflow velocity v. Such an experiment can include applying airflow across the thermistor at different flow rates and at alternating temperatures (e.g., room temperature between about 20° C. and about 25° C. to simulate inhalation and air temperature between 30° C. and 40° C. to simulate exhalation). A curve-fitting procedure can be employed to generate a polynomial or another function of T, $\dot{T}$, and $T_A$. Once G(v) is known, airflow velocity v can be estimated from $$\frac{\dot{T}}{(T_A - T)}.$$

Thus, continuous measurement of thermistor temperature T and $\dot{T}$ and periodically updating room temperature $T_A$ can be employed to obtain airflow velocity v once an expression of G(v) is available.

In alternative embodiments, it can be assumed that the relationship between rate of heating of the thermistor and the airflow velocity v and temperature is more complex than the model expressed in Equation 3. Therefore, a more complex experiment and data fitting can be performed. Thermistor temperature T and room temperature $T_A$ can be measured at different values of airflow velocity v and temperatures and curve fitting can be used to relate the airflow velocity v to the measured data (Equation 6):

$$v = f(T, \dot{T}, \ddot{T}, T_A). \quad (6)$$

where $\ddot{T}$ is the rate of change of $\dot{T}$.

In any of the above-described embodiments, a thermistor can be configured to determine air velocity v when it is not in steady state. As an example, the thermistor can have a time constant that is greater than the cooling portion of the respiration cycle.

Figure 6:
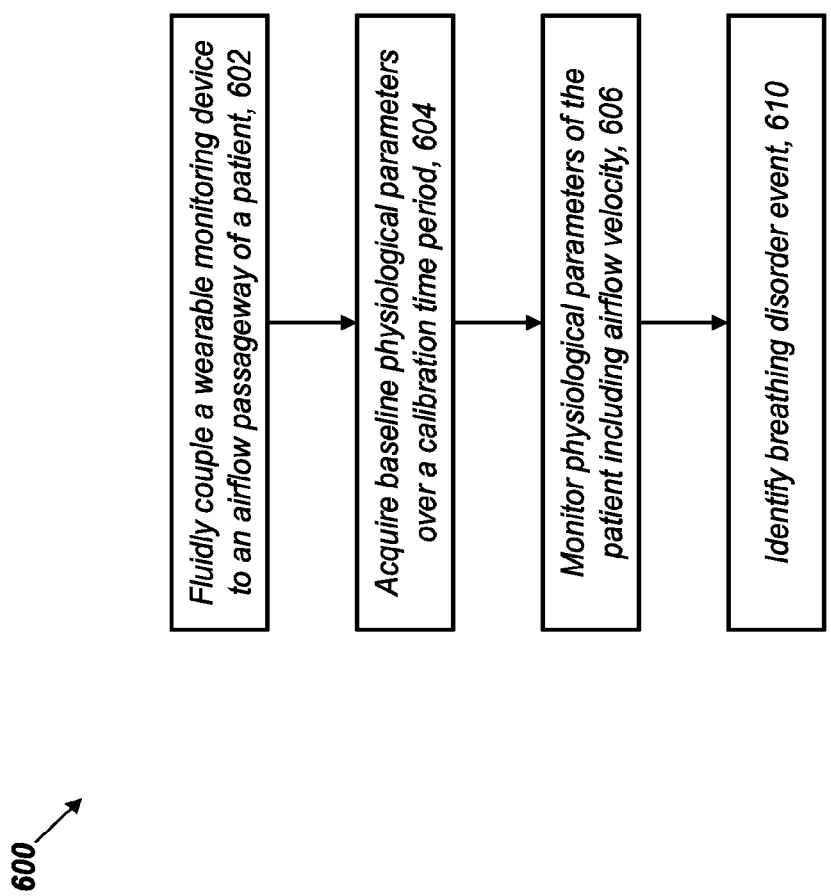
FIG. 6 is a flow diagram illustrating one exemplary embodiment of a method for identifying breathing disorders.

FIG. 6 is a flow diagram illustrating one exemplary embodiment of a method 600 for determining a sleep disorder from measurement of acquired physiological parameters, such as oral and/or nasal airflow. Embodiments of the method 600 are discussed below with reference to FIG. 2, however, the method 600 can be applied to any embodiments disclosed herein (e.g., wearable monitoring devices 300, 400, 500 of FIGS. 3-5). As shown in FIG. 6, the method 600 includes operations 602-610. However, a person skilled in the art will appreciate that embodiments of the method can include greater or fewer operations and that the operations can be performed in an order different than illustrated in FIG. 6.

In operation 602, a wearable monitoring device (e.g., 204) can be coupled an airflow passageway of a patient (e.g., 202) to perform a sleep study. In an embodiment, the wearable monitoring device can be coupled to the patient across the nasal septum, above the columella as previously discussed. So positioned, sensors (e.g., 310a, 310b) of the wearable monitoring device 204 can be positioned in thermal communication with respiratory airflow, such as oral or nasal airflow).

Subsequently, in operation 604, a calibration can be performed for an individual patient. The calibration can include acquiring baseline physiological parameters of the patient over a preselected calibration time duration. Physiological parameters acquired during the calibration time period can include but not limited to, one or more of breathing rate, breath volume (e.g., mean breath volume), airflow velocity (e.g., mean airflow velocity), sleep sounds (e.g., snoring), and breathing time. As an example, the baseline physiological parameters can be acquired over a period of about 10 breaths.

In operation 606, the one or more physiological parameters be monitored measured physiological parameters of the patient can be monitored and analyzed to identify at least one breathing event and/or breathing disorder. Such events and breathing disorders can include, but are not limited to, apnea events, hypopnea events, airflow velocity, snoring sounds, breath time, blood oxygen saturation, and the like and any combinations thereof.

In certain embodiments, the physiological parameters can include airflow velocity and blood oxygen saturation. Airflow velocity monitoring can be performed using one or more airflow sensors in the form of a thermistor (e.g., 310a, 310b). As discussed above, one or more thermistors can be placed in an airflow path being assessed (e.g., nasal airflow path, oral airflow path, etc.) when the wearable monitoring device 204 is coupled to an airflow pathway of the patient 202. Airflow velocity can be determined by allowing the thermistor to heat from air expired at body temperature along the airflow path being measured and thereafter monitoring cooling of the thermistor during inspiration of the breathing cycle along the same airflow path. Monitoring can include measuring a rate of temperature change of the thermistor and a temperature difference during inhalation by either calculating a conductance of heat flow between the thermistor's mass and the airflow or by analyzing the temperature dynamics during cooling of the thermistor, as discussed above.

Blood oxygen saturation monitoring can be performed using a pulse oximeter sensor (e.g., 312). The pulse oximeter sensor (e.g., 312) can be positioned at about vasculature across the nasal septum, where the wearable monitoring device is coupled to the patient 202. The pulse oximeter sensor 312 can determine blood oxygen saturation from vasculature of the nasal septum. The pulse oximeter sensor 312 can also determine the user's heart rate.

In operation 610, a sleep disorder event can identified from the airflow velocity, alone or in combination with blood oxygen saturation and/or other monitored physiological parameters. Sleep disorder events can include, but are not limited to, apnea, hypopnea, and combinations thereof. Identification of sleep disorder events can be performed by the wearable monitoring device 204 or another computing device (e.g., 210). As an example, a patient's sleep disorder event can be identified by abstracting a hypnogram and/or assessing the patient's apnea-hypopnea index score using physiological parameters acquired provided by the sensors 310a, 310b, 312. In the event that a sleep disorder event is identified, the identification can be communicated a computing device (e.g., 210) for further analysis.

Optionally sleep disorder analysis may be performed "offline" following the sleep study.

Determination of Core Body Temperature with Thermistors

In other embodiments, a method for determining core body temperature with a thermistor-based sensor (e.g., devices 204, 300, 400, 500) can be provided based upon temperature measurements acquired from respiration airflow. The method can include placing the sensor within a respiratory airflow path and acquiring temperature measurements of airflow during both inspiration and expiration. This monitoring can include measurement of the rate of change of temperature of a thermistor over time (e.g., $\dot{T}$) and the difference between the temperature of the thermistor T and the temperature of inhaled air $T_A$.

The method can also include equating the integral of inspiration and expiration. This can be described by Equation 7, below, where at equilibrium, the volume of air inhaled is equal to the volume of air exhaled:

$$\int_{inspiration} vdt = \int_{expiration} vdt \qquad (7)$$

An optimization process can be employed to facilitate solving Equation 7 to determine the value of core body temperature that satisfies the steady-state requirement expressed in Equation 7. The optimization process can begin with an estimate of core body temperature that is varied until the equilibrium satisfying Equation 7 is found.

Within the context of this application the term "about," "substantially," or "approximately," in reference to a measurement, data range, sizing or the like refers to a measurement with deviation of +/−10%.

Embodiments of the above-described systems, devices, and methods can be implemented in digital electronic circuitry, in computer hardware, firmware, and/or software. The implementation can be as a computer program product. The implementation can, for example, be in a machine-readable storage device, for execution by, or to control the operation of, data processing apparatus. The implementation can, for example, be a programmable processor, a computer, and/or multiple computers.

A computer program can be written in any form of programming language, including compiled and/or interpreted languages, and the computer program can be deployed in any form, including as a stand-alone program or as a subroutine, element, and/or other unit suitable for use in a computing environment. A computer program can be deployed to be executed on one computer or on multiple computers at one site.

Method steps can be performed by one or more programmable processors executing a computer program to perform functions of the invention by operating on input data and generating output. Method steps can also be performed by and an apparatus can be implemented as special purpose logic circuitry. The circuitry can, for example, be a FPGA (field programmable gate array) and/or an ASIC (application-specific integrated circuit). Subroutines and software agents can refer to portions of the computer program, the processor, the special circuitry, software, and/or hardware that implement that functionality.

Processors suitable for the execution of a computer program include, by way of example, both general and special purpose microprocessors, and any one or more processors of any kind of digital computer. Generally, a processor receives instructions and data from a read-only memory or a random access memory or both. The essential elements of a computer are a processor for executing instructions and one or more memory devices for storing instructions and data. Generally, a computer can include, can be operatively coupled to receive data from and/or transfer data to one or more mass storage devices for storing data (e.g., magnetic, magneto-optical disks, or optical disks).

Data transmission and instructions can also occur over a communications network. Information carriers suitable for embodying computer program instructions and data include all forms of non-volatile memory, including by way of example semiconductor memory devices. The information carriers can, for example, be EPROM, EEPROM, flash memory devices, magnetic disks, internal hard disks, removable disks, magneto-optical disks, CD-ROM, and/or DVD-ROM disks. The processor and the memory can be supplemented by, and/or incorporated in special purpose logic circuitry.

To provide for interaction with a user, the above described techniques can be implemented on a computer having a display device. The display device can, for example, be a cathode ray tube (CRT) and/or a liquid crystal display (LCD) monitor. The interaction with a user can, for example, be a display of information to the user and a keyboard and a pointing device (e.g., a mouse or a trackball) by which the user can provide input to the computer (e.g., interact with a user interface element). Other kinds of devices can be used to provide for interaction with a user. Other devices can, for example, be feedback provided to the user in any form of sensory feedback (e.g., visual feedback, auditory feedback, or tactile feedback). Input from the user can, for example, be received in any form, including acoustic, speech, and/or tactile input.

The above described techniques can be implemented in a distributed computing system that includes a back-end component. The back-end component can, for example, be a data server, a middleware component, and/or an application server. The above described techniques can be implemented in a distributing computing system that includes a front-end component. The front-end component can, for example, be a client computer having a graphical user interface, a Web browser through which a user can interact with an example implementation, and/or other graphical user interfaces for a transmitting device. The components of the system can be interconnected by any form or medium of digital data communication (e.g., a communication network). Examples of communication networks include a local area network (LAN), a wide area network (WAN), the Internet, wired networks, and/or wireless networks.

The system can include clients and servers. A client and a server are generally remote from each other and typically interact through a communication network. The relationship of client and server arises by virtue of computer programs running on the respective computers and having a client-server relationship to each other.

Packet-based networks can include, for example, the Internet, a carrier internet protocol (IP) network (e.g., local area network (LAN), wide area network (WAN), campus area network (CAN), metropolitan area network (MAN), home area network (HAN)), a private IP network, an IP private branch exchange (IPBX), a wireless network (e.g., radio access network (RAN), IEEE 802.11 network, IEEE 802.16 network, general packet radio service (GPRS) network, HiperLAN), and/or other packet-based networks. Circuit-based networks can include, for example, the public switched telephone network (PSTN), a private branch exchange (PBX), a wireless network (e.g., RAN, Bluetooth®, code-division multiple access (CDMA) network, time division multiple access (TDMA) network, global system for mobile communications (GSM) network), and/or other circuit-based networks.

The transmitting device can include, for example, a computer, a computer with a browser device, a telephone, an IP phone, a mobile device (e.g., cellular phone, personal digital assistant (PDA) device, laptop computer, electronic mail device), and/or other communication devices. The browser device includes, for example, a computer (e.g., desktop computer, laptop computer) with a World Wide Web browser (e.g., Microsoft® Internet Explorer® available from Microsoft Corporation, Mozilla® Firefox available from Mozilla Corporation, Chrome Browser available from Google®). The mobile computing device includes, for example, a Blackberry®.

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the claimed embodiments. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

It must be noted that, as used herein and in the appended claims, the singular forms "a", "an", and "the" include plural reference unless the context clearly dictates otherwise. Thus, for example, reference to "a cell" includes a plurality of such cells and equivalents thereof known to those skilled in the art, and so forth. As well, the terms "a" (or "an"), "one or more" and "at least one" can be used interchangeably herein. It is also to be noted that the terms "comprising", "including", and "having" can be used interchangeably. The expression "of any of claims XX-YY" (wherein XX and YY refer to claim numbers) is intended to provide a multiple dependent claim in the alternative form, and in some embodiments is interchangeable with the expression "as in any one of claims XX-YY."

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. Nothing herein is to be construed as an admission that the invention is not entitled to antedate such disclosure by virtue of prior invention.

Every formulation or combination of components described or exemplified herein can be used to practice the invention, unless otherwise stated.

Whenever a range is given in the specification, for example, a temperature range, a time range, or a composition or concentration range, all intermediate ranges and sub-ranges, as well as all individual values included in the ranges given are intended to be included in the disclosure. As used herein, ranges specifically include the values provided as endpoint values of the range. For example, a range of 1 to 100 specifically includes the end point values of 1 and 100. It will be understood that any sub-ranges or individual values in a range or sub-range that are included in the description herein can be excluded from the claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

A person skilled in the art will appreciate further features and advantages of the invention based on the above-described embodiments. Accordingly, the invention is not to be limited by what has been particularly shown and described, except as indicated by the appended claims. All publications and references cited herein are expressly incorporated by reference in their entirety.

The invention claimed is:

1. A method for determining a velocity of respiratory airflow of a patient, the method comprising:
    (a) applying airflow across a thermistor at different flow rates and at alternating temperatures to simulate inhalation and exhalation;
    (b) measuring, by the thermistor, temporal temperature T and calculating a rate of change of temperature $\dot{T}$;
    (c) employing, by at least one processor, a curve-fitting procedure to the rate of change of temperature T of the thermistor to generate an empirical function G(v) of respiratory airflow velocity v;
    (d) receiving, by the at least one processor, measurements from the thermistor when positioned in fluid communication with a respiratory airflow of a patient to obtain temporal temperature T of the respiratory airflow of the patient;
    (e) continuously measuring thermistor temperature T and calculating $\dot{T}$ from the thermistor when positioned in fluid communication with the respiratory airflow of the patient, to obtain airflow velocity v of the respiratory airflow of the patient based on G(v);
    (f) assessing, by the at least one processor, a breathing disorder of the patient for the patient based on the airflow velocity v; and
    (g) displaying by the at least one processor, on a display, the results of the assessment,
    wherein G(v) is expressed as $$G(v) = \frac{1}{R(v)C_T} = \frac{\dot{T}}{(T_A - T)}$$

and wherein $\dot{T}_A$ is a temperature surrounding a system comprising the thermistor, $C_T$ is a constant and, R(v) is the heat transfer resistance of the thermistor.

2. The method of claim 1, wherein R(v) is calculated from constants associated with the thermistor.

3. The method of claim 1, wherein receiving, by said at least one processor, measurements is from the thermistor and one additional thermistor positioned in fluid communication with one or more respiratory airflows.

4. The method of claim 1, wherein receiving, by said at least one processor, measurements is from the thermistor and one additional thermistor, each thermistor positioned in fluid communication with a different respiratory airflow.

5. The method of claim 4, wherein one of the thermistor and the one additional thermistor is in fluid communication with the nose of the patient and the other thermistor is in fluid communication with the mouth of the patient.

6. A system for determining a velocity of respiratory airflow of a patient, the system comprising:
    a thermistor; and
    at least one processor configured to:
    (a) apply airflow across the thermistor at different flow rates and at alternating temperatures to simulate inhalation and exhalation;
    (b) measure temporal temperature T of the thermistor and calculate a rate of change of temperature T of the thermistor;

(c) employ a curve-fitting procedure to the rate of change of temperature $\dot{T}$ of the thermistor to generate an empirical function G(v) of respiratory airflow velocity v;

(d) continuously measure thermistor temperature T and calculate $\dot{T}$ when the thermistor is positioned in fluid communication with a respiratory airflow of the patient, to obtain airflow velocity v of the respiratory airflow of the patient based on G(v);

(e) assess a breathing disorder of the patient for the patient based on the airflow velocity v; and (f) display, on a display, the results of the assessment;

wherein G(v) is expressed as $$G(v) = \frac{1}{R(v)C_T} = \frac{\dot{T}}{(T_A - T)};$$

and wherein $T_A$ is a temperature surrounding the system, $C_T$ is a constant and, R(v) is the heat resistance of the thermistor.

7. The system of claim 6, wherein R(v) is calculated from constants associated with the thermistor.

8. The system of claim 6, wherein receiving, by said at least one processor, measurements is from the thermistor and one additional thermistor of the system, each thermistor positioned in fluid communication with one or more respiratory airflows.

9. The system of claim 6, wherein receiving, by said at least one processor, measurements is from the thermistor and one additional thermistor of the system, each thermistor positioned in fluid communication with a different respiratory airflow.

10. The system of claim 9, wherein one of the thermistor and the one additional thermistor is in fluid communication with the nose of the patient and the other thermistor is in fluid communication with the mouth of the patient.

* * * * *